United States Patent [19]
Ichikawa et al.

[11] 3,975,441
[45] Aug. 17, 1976

[54] PROCESS FOR RECOVERING PURIFIED 4-HYDROXY-2,4,6-TRIMETHYL-2,5-CYCLOHEXADIENE-1-ONE

[75] Inventors: Yataro Ichikawa; Yoshiyuki Yamanaka; Nobuo Suzuki; Hideki Tsuruta, all of Iwakuni, Japan

[73] Assignee: Teijin Limited, Osaka, Japan

[22] Filed: Apr. 29, 1974

[21] Appl. No.: 464,950

[30] Foreign Application Priority Data
May 7, 1973 Japan.............................. 48-49668

[52] U.S. Cl.............................. 260/586 R; 203/91; 260/586 P
[51] Int. Cl.$^2$.................... C07C 45/24; C07C 29/26
[58] Field of Search..................... 260/586 R, 586 P; 203/91

[56] References Cited
UNITED STATES PATENTS 3,462,348  8/1969  Wellman et al................. 260/586 R
3,758,596  9/1973  Reed et al....................... 260/586 R
3,840,023  10/1974 Demole........................... 260/586 R

OTHER PUBLICATIONS

Adler et al., "Acta. Chem. Scanda.", vol. 14, pp. 1580–1596 (1960).

Bamberger et al., "Ber.", vol. 33, p. 3636, (1900).

*Primary Examiner*—Norman Morgenstern
*Attorney, Agent, or Firm*—Sherman & Shalloway

[57] ABSTRACT

A process for recovering purified 4-hydroxy-2,4,6-trimethyl-2,5-cyclohexadiene-1-one by distilling crude 4-hydroxy-,2,4,6-trimethyl-2,5-cyclohexadien-1-one. Preferably, the distillation is performed at a temperature of 40° to 250°C. using crude 4-hydroxy-2,4,6-trimethyl-2,5-cyclohexadien-1-one having a pH of 4 to 11.5. Thus, 4-hydroxy-2,4,6-trimethyl-2,5-cyclohexadien-1-one of high purity and reduced coloration can be recovered at a high recovery ratio.

4 Claims, No Drawings

PROCESS FOR RECOVERING PURIFIED 4-HYDROXY-2,4,6-TRIMETHYL-2,5-CYCLOHEXADIENE-1-ONE

This invention relates to a process for separating and recovering purified 4-hydroxy-2,4,6-trimethyl-2,5-cyclohexadien-1-on. More specifically, this invention relates to a process for separating and recovering a fraction of purified 4-hydroxy-2,4,6-trimethyl-2,5-cyclohexadien-1-one by distilling crude 4-hydroxy-2,4,6-trimethyl-2,5-cyclohexadien-1-one.

4-Hydroxy-2,4,6-trimethyl-2,5-cyclohexadien-1-one (to be referred to simply as TMCH) has a structure expressed by the following formula

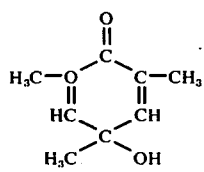

The following methods have previously been known for the preparation of TMCH.

1. Oxidation of 2,4,6-trimethylphenol generally called mesitol (to be referred to as TMP). Two specific procedures are known to perform this method.

1-a. Reaction of TMP with a peracid such as Caro's acid ($H_2SO_5$) to form TMCH. This procedure is shown by the following reaction equation.

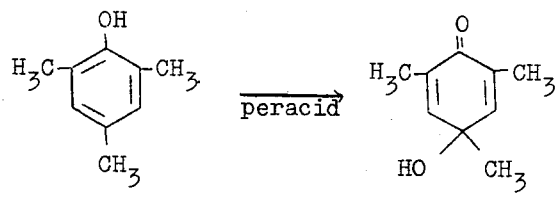

1-b. The method for obtaining TMCH by oxidizing TMP with molecular oxygen, which was proposed by the inventors of the present application prior to the present invention. In this method, the use of a basic substance such as sodium hydroxide or potassium hydroxide as a catalyst is preferred.

2. Method comprising the rearrangement of 1-hydroxyamino-2,4,6-trimethylbenzene as shown by the following equation.

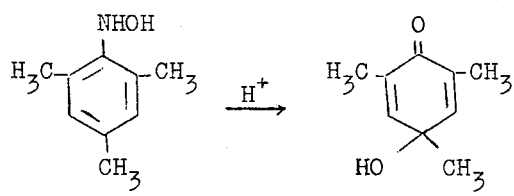

This reaction is generally carried out in an aqueous solution of a mineral acid such as sulfuric acid.

The reaction mixture produced by the above methods or crude TMCH separated from it contains the unreacted starting material, the reaction intermediate product, the catalyst and various impurities ascribable to the reaction. Such an impure TMCH is unsuitable as a product or as a reagent for other reactions. For the purification of such crude TMCH, (a) a recrystallizing method using water [Journal of the Society of Organic Syntheses, Japan, 25, 252 (1967)] and (b) a recrystallizing method using petroleum ether [Ber. 33, 3600–3658 (1900)] have previously been known. Investigations of the present inventors have shown that by either of these recrystallizing methods, TMCH of fully satisfactory purity cannot be obtained, and moreover, the ratio of its recovery is unsatisfactory.

Accordingly, an object of this invention is to provide a process for recovering purified TMCH of high purity at a high recovery ratio by purifying crude TMCH.

Another object of this invention is to provide a process for separating and recovering purified TMCH of high purity and reduced coloration at a high recovery ratio from a reaction mixture containing crude TMCH.

Other objects and advantages of this invention will become apparent from the following description.

The objects and advantages of this invention can be achieved by distilling crude TMCH and recovering purified TMCH as a fraction. It was quite unexpected that in spite of the fact that TMCH is structurally very unstable as is seen from the structural formula given herein above, the distillation of crude TMCH gives TMCH of high purity and reduced coloration at a high recovery ratio.

Accordingly, this invention can be applied not only to the purification of crude TMCH, but also to the separation of TMCH from a reaction mixture containing TMCH.

The crude TMCH to be used in this invention may be those which are produced by any methods. For example, the process of this invention can be applied to the purification of crude TMCH produced by any conventional method, such as those described in (1-a), (1-b), and (2), or the separation and recovery of purified TMCH from the reaction mixture produced by such conventional methods.

The purifying method or separating and purifying method of this invention is preferably applied to crude TMCH produced by the oxidation of TMP in (1-a) or (1-b), or to a reaction mixture containing it, since this results in the recovery of high purity TMCH of very much reduced coloration at a high recovery ratio.

However, the present invention can be applied to the reaction mixtures produced by any methods such as (1-a), (1-b) or (2), or to any crude TMCH obtained by concentrating such reaction mixtures or by separation therefrom, and the reaction mixtures or the crude TMCH may contain TMCH in any proportions.

For example, when the reaction of forming crude TMCH is carried out in the molten state, the crude TMCH obtained can be directly submitted to the process of this invention. Or it may be pre-treated by the following procedure.

When the reaction mixture is a homogeneous solution, a liquid-liquid mixture or a solid-liquid solution, the crude TMCH is first separated from the reaction mixture by conventional methods such as extracting with solvent, recrystallization or the evaporation of the solvent in the reaction mixture, and then purified. Furthermore, it is possible to subject the reaction mixture first to the conventional recrystallization, and then to the purifying process of this invention.

According to this invention, the crude TMCH described above is purified by introducing it into a purifying apparatus in the gaseous or liquid state and distilling it. The temperature at which the crude TMCH is purified by distillation is 40° to 250°C., preferably 60° to 200°C. It is most advantageous to perform the distillation in accordance with this invention at 80° to 180°C.

The TMCH has a melting point of 44.0°C. and a vapor pressure (mmHg abs.) of 0.6 at 80°C., 7.0 at 120°C., 92.0 at 180°C. and 311 at 220°C.

As can be seen from the vapor pressures of TMCH for particular temperatures given above, extremely low operating pressures are required at such low temperatures, and this is commercially disadvantageous. Furthermore, at such low temperatures, 2,4,6-trimethyl phenol (TMP), if present in the crude TMCH, would be solidified in the distillation still, and this makes the distilling operation difficult.

TMCH can also be distilled at temperatures higher than 200°C. or even higher than 250°C. When the upper limit of the distillation temperature exceeds 180°C., especially 200°C., above all 250°C., the operating pressure must be made higher to facilitate the distilling operation. When this happens, the deterioration of TMCH becomes very noticeable, the recovery ratio of the TMCH is reduced, and the TMCH is colored.

Accordingly, the distillation of TMCH in accordance with this invention is preferably carried out at a temperature within the above-specified range.

It is especially important to limit the temperature of the bottom of the distillation still to the range specified.

When the distilling temperature is relatively high within the specified range, especially when the distilling temperature exceeds 150°C., especially 180°C., the time during which the crude TMCH or a mixture containing it is exposed to such temperatures should be shortened as much as possible, in order to obtain TMCH of high purity and reduced coloration at a high recovery ratio. In order to achieve this, the use of a distillation still of the film type or flush type to be described is advantageous.

The pressure at which the distillation in accordance with this invention is performed varies according to the components of the starting crude TMCH, the proportions of the components, the desired purity of TMCH, and the distilling temperature, but may be any pressure at which the distillation and separation of TMCH can be performed at the above-specified temperature.

The apparatus for performing the distillation in accordance with the present invention may be of any conventional type, such as the tray type, packed type, film type, or flush type. The distillation can be performed either batchwise or continuously.

We have also found that when the crude TMCH has a pH of 4 to 11.5, preferably 4.5 to 11, above all 5 to 11 in distilling it or a composition containing it, high purity TMCH of extremely reduced coloration can be obtained at a higher recovery ratio and by a stable distilling operation. Thus, the use of crude TMCH or a composition containing it which has this pH range is especially advantageous.

The pH of the crude TMCH is based on a pH value measured on a solution of 4 parts by weight (for example, 4 g) of the crude TMCH in an aqueous methanol solution consisting of 3 parts by weight (for example, 3 g) of water and 10 parts by weight (for example, 10 g) of methanol.

If crude TMCH having a pH value, measured by this standard measuring method, outside the above-specified range is distilled, there is a general tendency that the degree of coloration of the purified TMCH obtained as a fraction increases, its purity is reduced, and the recovery ratio of the purified TMCH decreases, even when the distilling temperature is within the above-specified range.

The reaction mixture containing crude TMCH obtained by the conventional methods contains a considerable amount of acid or alkali because, for example, a peracid is used in the method (1-a), a basic substance is used as a catalyst in the method (1-b), or the method (2) is generally carried out in an aqueous solution of a mineral acid. Therefore, the reaction mixture has a pH value, as measured by the above-mentioned standard measuring method, of less than 4 or more than 12.

When such a reaction mixture is simply concentrated, or treated with an organic solvent such as petroleum ether by the above conventional method to crystallize out TMCH or the crude TMCH is treated with water, the resulting TMCH treated only once by any of these treating methods still contains the acid or alkali in a considerable amount. This frequently leads to the failure of obtaining purified TMCH of fully reduced coloration even when the crude TMCH is purified by the process of this invention.

However, when the crude TMCH is distilled in accordance with this invention after removing the acid or alkali from it until its pH value becomes 4 to 11.5, preferably 4.5 to 11, above all 5 to 11, high purity TMCH of extremely reduced coloration can be obtained at a higher recovery ratio.

A neutralization method and an extraction method can, for example, be employed in order to obtain crude TMCH or a composition containing it which has a pH value as specified above by removing the acid or alkali or reducing its content.

The neutralization method comprises neutralizing the reaction mixture containing crude TMCH or its treated product with alkali or acid when it contains acid or alkali to adjust the pH of the crude TMCH, measured by the above standard measuring method, to the range specified above.

The extracting method includes two procedures. One procedure involves treating the reaction mixture with a suitable organic solvent to transfer TMCH into the organic solvent phase and leave the acid or alkali in the aqueous phase or in the extraction residue. The other involves treating the crude TMCH or its solution in an organic solvent with water or another aqueous medium to extract the acid or alkali with water or the aqueous medium, and separating and removing it from the crude TMCH or its organic solvent solution.

The extraction of TMCH with the above organic solvent and the treatment of it with water or other aqueous medium can be performed jointly a suitable number of times. Alternatively, these extracting methods can be combined with the above neutralization method. The extracting method using an organic solvent or an aqueous medium is preferred since this method makes it possible to remove coloring components or other impurities from the crude TMCH in advance.

The removal of acid or alkali from crude TMCH or the reduction of its content may be carried out by any other methods than the neutralization method or the extraction method. The above advantages can be achieved by distilling crude TMCH having a pH value of 4 to 11.5, preferably 4.5 to 11 or a composition containing it in the manner described above. Accordingly, even when the crude TMCH having such a pH range is distilled at a higher temperature, it is possible to recover high purity TMCH of reduced coloration at a high recovery ratio. This makes it possible to recover a greater amount of high purity TMCH within a shorter period of time.

Thus, according to the present invention described above, TMCH of very high purity can be easily recovered at a high recovery ratio, and can be used either as such or can be converted to trimethyl hydroquinone by rearrangement.

The following Examples illustrate the present invention in greater detail, but it should be understood that the invention is in no way limited by them.

The pH value of the crude TMCH, and the optical density and purity of the purified TMCH were measured by the following methods.

pH 4 grams of a sample was dissolved in an aqueous methanol solution consisting of 10 gr. of methanol and 3 gr. of water, and the pH of the solution was measured.

Optical density 0.5 gr. of a sample was dissolved in ethanol to make the amount of the solution 25 ml. The absorbance of the resulting solution was measured at a wavelength of 400 m$\mu$ with a cell length of 1 cm.

Purity

Determined by gas-chromatographic analysis.

The material balance and the ratio of recovery were calculated from the following equations.

Material balance of TMCH = $\dfrac{\text{Total weight of TMCH in the distillate and the distillation residue}}{\text{Weight of TMCH in the crude TMCH charge}} \times 100$ Material balance of TMP = $\dfrac{\text{Total weight of TMP in the distillate and the distillation residue}}{\text{Weight of TMP in the crude TMCH charge}} \times 100$ Recovery ratio of TMCH = $\dfrac{\text{Weight of purified TMCH distilled out per unit time}}{\text{Weight of TMCH in the crude TMCH charged, per unit time}} \times 100$

EXAMPLE 1

100 g of crude TMCH (containing 11.64% by weight of 2,4,6-trimethylphenol, and 87.20% by weight of TMCH and having a pH of 6.5 and an optical density of 0.110) obtained by oxidizing 2,4,6-trimethylphenol with molecular oxygen was charged in a concentric precise fractional distillation apparatus, and distilled, and the purified TMCH separated, under the conditions shown in Table 1 below.

The distillation residue was black in color, and weighed 2.3 g. It was analyzed and found to contain 0.1% by weight of 2,4,6-trimethylphenol and 2.1% by weight of TMCH and have an optical density of 2.

A white solid weighing 0.7 g deposited in a vacuum trap, which was found to be 2,4,6-trimethylphenol.

The material balance was 99.9% by weight for TMP, and was 99.9% by weight for TMCH.

Table 1

| Summation weight of the distillate (g) | Temperature (°C.) Top of the still | Bottom of the still | Pressure at the top of distillation still (mmHg. abs) | Analysis of the distillate TMP (wt. %) | TMCH (wt. %) | Optical density |
|---|---|---|---|---|---|---|
| 0.4 | 100 | 130 | 9 | 96.1 | 3.9 | 0.075 |
| 7.0 | 104 | 130 | 6 | 61.2 | 38.7 | 0.220 |
| 23.8 | 120 | 133 | 5 | 20.0 | 80.0 | 0.130 |
| 54.7 | 123 | 135 | 5 | 6.4 | 93.7 | 0.073 |
| 83.0 | 125 | 139 | 5 | 0.4 | 99.6 | 0.064 |
| 97.0 | 116 | 144–180 | 4–5 | 0.06 | 99.9 | 0.088 |

EXAMPLE 2

An aqueous solution of a reaction product containing crude TMCH obtained by oxidizing 2,4,6-trimethylphenol with molecular oxygen was placed in a flask, and benzene was added. The mixture was stirred at room temperature under atmospheric pressure. Then, the stirring was stopped, and the mixture was separated into two liquid phases. The upper benzene phase was withdrawn, and subjected to a rotary evaporator to evaporate and remove benzene to obtain crude TMCH. The crude TMCH was analyzed and found to contain 31.8% by weight of 2,4,6-trimethylphenol, and 65.4% by weight of TMCH and have a pH of 6.7 and an optical density of 0.103.

503 g of the crude TMCH was charged into a Widmer distillation device, and distilled. The results are shown in Table 2 below.

The distillation residue weighed 20 g, and there were formed 0.7% by weight of 2,4,6-trimethylphenol and 31.5% by weight of TMCH. The optical density was 2.

The material balance was 100.0% by weight for TMP, and 99.9% by weight for TMCH.

Table 2

| Summation weight of the distillate (g) | Temperature (°C.) Top of the still | Bottom of the still | Pressure at the top of distillation still (mmHg. abs) | Analysis of the distillate (wt. %) | (wt. %) | Optical density |
|---|---|---|---|---|---|---|
| 125.0 | 81–92 | 122–130 | 2 | 88.4 | 11.6 | 0.095 |
| 190.0 | 87–92 | 125–129 | 2 | 53.7 | 46.3 | 0.134 |

Table 2-continued

| Summation weight of the distillate (g) | Temperature (°C.) Top of the still | Temperature (°C.) Bottom of the still | Pressure at the top of distillation still (mmHg. abs) | Analysis of the distillate (wt. %) | Analysis of the distillate (wt. %) | Optical density |
|---|---|---|---|---|---|---|
| 223.6 | 87–91 | 125–126 | 2 | 22.2 | 77.7 | 0.095 |
| 290.4 | 91 | 125–126 | 2 | 8.0 | 92.0 | 0.072 |
| 347.9 | 91 | 125 | 2 | 1.9 | 98.2 | 0.068 |
| 390.9 | 90 | 125–126 | 2 | 0.5 | 99.4 | 0.069 |
| 482.4 | 91–92 | 127–151 | 2 | 0.3 | 99.7 | 0.068 |

EXAMPLE 3

200 g of crude TMCH obtained by oxidizing 2,4,6-trimethylphenol (TMP) with molecular oxygen (2,4,6-trimethylphenol 14.8% by weight, TMCH 78.2% by weight, optical density 0.142, pH 6.6) was charged into the same distillation device as in Example 2, and distilled. The results are shown in Table 3.

The distillation residue weighed 20.5 g, and was found to contain 0.30% by weight of TMP and 27.1% by weight of TMCH and have an optical density of 2. The material balance was 100.0% by weight for TMP, and 99.3% by weight for TMCH.

Table 3

| Samples Nos. | Weight of the distillate (g) | Temperature (°C.) Bottom of the still | Temperature (°C.) Top of the still | Pressure at the top of the still (mmHg. abs) | TMP (wt. %) | TMCH (wt. %) | Optical density |
|---|---|---|---|---|---|---|---|
| 1 | 16.5 | 146–147 | 125–130 | 29 | 76.8 | 23.2 | 0.131 |
| 2 | 21.0 | 150 | 134 | 30 | 52.0 | 48.0 | 0.140 |
| 3 | 10.5 | 150 | 136 | 30 | 30.8 | 69.2 | 0.141 |
| 4 | 13.5 | 152 | 144 | 31 | 10.7 | 89.3 | 0.102 |
| 5 | 15.0 | 153 | 144 | 31 | 5.0 | 95.5 | 0.088 |
| 6 | 21.5 | 153 | 145 | 30 | 1.9 | 98.1 | 0.086 |
| 7 | 20.0 | 153 | 144 | 29 | 0.6 | 99.4 | 0.085 |
| 8 | 24.5 | 154 | 145 | 30 | 0.4 | 99.6 | 0.078 |
| 9 | 21.0 | 156 | 147 | 29 | 0.4 | 99.6 | 0.075 |
| 10 | 16.0 | 156–175 | 148 | 30 | 0.3 | 99.7 | 0.086 |

EXAMPLE 4

180 g of the same crude TMCH as used in Example 3 was distilled under the conditions shown in Table 4 using the same distillation device as in Example 2. The results are shown in Table 4.

The distillation residue weighed 21.5 g, and found to contain 0.3% by weight of TMP and 30.8% by weight of TMCH and have an optical density of 2. The material balance was 102.8%, by weight for TMP and was 97.9% by weight for TMCH.

Table 4

| Samples Nos. | Weight of the distillate (g) | Temperature (°C.) Bottom of the still | Temperature (°C.) Top of the still | Pressure at the top of the still (mmHg. abs) | TMP (wt. %) | TMCH (wt. %) | Optical density |
|---|---|---|---|---|---|---|---|
| 1 | 13.5 | 185 | 110 | 90 | 50.1 | 49.9 | 0.090 |
| 2 | 14.5 | 180 | 110 | 90 | 42.5 | 57.5 | 0.099 |
| 3 | 15.0 | 182 | 110–118 | 90 | 38.6 | 61.4 | 0.065 |
| 4 | 14.0 | 185 | 118 | 90 | 30.7 | 69.3 | 0.073 |
| 5 | 14.0 | 185 | 140 | 90 | 12.7 | 87.3 | 0.077 |
| 6 | 13.5 | 185 | 150 | 92 | 6.2 | 93.8 | 0.075 |
| 7 | 16.5 | 183 | 175 | 92 | 4.5 | 95.5 | 0.091 |
| 8 | 25.5 | 185 | 178 | 90 | 1.9 | 98.1 | 0.100 |
| 9 | 17.0 | 185–188 | 180 | 90 | 0.7 | 99.3 | 0.084 |
| 10 | 15.0 | 190–195 | 179 | 90 | 2.2 | 97.8 | 0.137 |

EXAMPLE 5

200 g of the same crude TMCH (2,4,6-trimethyl phenol 14.5% by weight, TMCH 81.1% by weight, optical density 0.166, pH 6.7) as used in Example 2 was distilled in the same way as in Example 3. The results are shown in Table 5.

Table 5

| Samples Nos. | Weight of the distillate (g) | Temperature (°C.) Bottom of the still | Temperature (°C.) Top of the still | Pressure at the top of the still (mmHg. abs) | TMP (wt. %) | TMCH (wt. %) | Optical density |
|---|---|---|---|---|---|---|---|
| 1 | 12.0 | 183 | 160 | 120 | 49.6 | 50.4 | 0.089 |
| 2 | 18.0 | 188 | 165–180 | 130 | 61.4 | 38.6 | 0.072 |
| 3 | 18.5 | 192 | 185 | 130 | 32.0 | 68.0 | 0.071 |
| 4 | 20.5 | 194 | 187 | 140 | 19.5 | 80.5 | 0.075 |
| 5 | 18.5 | 198 | 190 | 148 | 13.2 | 86.8 | 0.090 |
| 6 | 16.5 | 199 | 192 | 150 | 6.2 | 93.8 | 0.101 |
| 7 | 21.0 | 200 | 193 | 150 | 5.0 | 94.5 | 0.114 |

Table 5-continued

| Samples Nos. | Weight of the distillate (g) | Temperature (°C.) Bottom of the still | Temperature (°C.) Top of the still | Pressure at the top of the still (mmHg. abs) | Analysis of the distillate TMP (wt. %) | Analysis of the distillate TMCH (wt. %) | Optical density |
|---|---|---|---|---|---|---|---|
| 8 | 20.0 | 203 | 193 | 150 | 2.4 | 97.6 | 0.105 |
| 9 | 18.5 | 205 | 192 | 150 | 3.0 | 97.0 | 0.136 |
| 10 | 14.5 | 205–219 | 180–190 | 150 | 2.5 | 97.5 | 0.146 |

The distillation residue weighed 22.0 g, and found to contain 0.3% by weight of TMP and 3.1% by weight of TMCH and have an optical density of 2.

The material balance was 113.4% by weight for TMP, and 89.9% by weight for TMCH.

EXAMPLE 6

This Example was for the purpose of determining the effect of pH on TMCH when it was maintained in the molten state.

4 g of purified TMCH was dissolved in an aqueous solution consisting of 10 g of methanol and 3 g of water, and a dilute aqueous solution of sodium hydroxide or a dilute aqueous solution of sulfulic acid was added by means of a pH meter, thereby to adjust the pH of the mixture to the values shown in Table 6 below. Then, this solution was subjected to a rotary evaporator to remove the methanol and water at room temperature under reduced pressure, to form TMCH in the molten state.

The TMCH was placed into a sealed glass tube after thorough purging with nitrogen, and then the glass tube was immersed for 4 hours in an oil bath held at 120°C.

The tube was then cooled to room temperature, and the contents of the tube were gas-chromatographed, and also analyzed for optical density. The results are shown in Table 6.

The purified TMCH used was analyzed and found to contain 0.10% by weight of 2,4,6-trimethylphenol and 99.90% by weight of TMCH and have an optical density of 0.066.

Table 6

| pH values adjusted | Gas-chromatographic analysis (wt.%) TMP | Gas-chromatographic analysis (wt.%) TMCH | Optical density |
|---|---|---|---|
| 0.7 | — | — | 2 |
| 2.0 | — | — | 2 |
| 3.0 | 16.30 | 3.54 | 2 |
| 4.0 | 4.12 | 74.07 | 0.195 |
| 4.5 | 2.11 | 92.00 | 0.098 |
| 5.1 | 0.24 | 99.66 | 0.070 |
| 6.0 | 0.24 | 99.76 | 0.067 |
| 6.7 | 0.25 | 99.75 | 0.072 |
| 7.0 | 0.25 | 99.75 | 0.069 |
| 7.9 | 0.25 | 99.75 | 0.070 |
| 8.9 | 0.24 | 99.76 | 0.071 |

Table 6-continued

| pH values adjusted | Gas-chromatographic analysis (wt.%) TMP | Gas-chromatographic analysis (wt.%) TMCH | Optical density |
|---|---|---|---|
| 9.9 | 0.24 | 99.76 | 0.081 |
| 10.9 | 0.22 | 99.78 | 0.092 |
| 11.5 | 0.55 | 75.77 | 0.202 |
| 12.0 | 0.78 | 25.23 | 2 |
| 13.0 | — | — | 2 |

EXAMPLE 7

130 g of crude TMCH (2,4,6-trimethylphenol 14.5% by weight, TMCH 81.3% by weight, optical density 0.170, pH 8.5) obtained by oxidizing TMP with molecular oxygen was distilled in the same way as in Example 2 using the same distillation device as used in Example 2. The results are shown in Table 7.

The distillation residue weighed 12.9 g, and found to contain traces of 2,4,6-trimethylphenol and 34.5% by weight of TMCH and have an optical density of 2. The material balance was 100.0% by weight for 2,4,6-trimethylphenol and 100.0% by weight for TMCH.

Table 7

| Samples Nos. | Weight of the distillate (g) | Temperature (°C.) Top of the still | Temperature (°C.) Bottom of the still | Pressure at the bottom of the still (mmHg, abs) | Analysis of the distillate TMP (wt. %) | Analysis of the distillate TMCH (wt. %) | Optical density |
|---|---|---|---|---|---|---|---|
| 1 | 16.2 | 89 | 114 | 5 | 93.0 | 7.0 | 0.146 |
| 2 | 6.7 | 99 | 116 | 5 | 35.8 | 64.2 | 0.276 |
| 3 | 9.0 | 101 | 116 | 5 | 6.9 | 93.1 | 0.117 |
| 4 | 11.3 | 102 | 116 | 5 | 2.6 | 97.4 | 0.086 |
| 5 | 13.4 | 103 | 119 | 5 | 1.3 | 98.7 | 0.084 |
| 6 | 15.3 | 105 | 119 | 5 | 0.8 | 99.2 | 0.084 |
| 7 | 13.8 | 105 | 119 | 5 | 0.6 | 99.4 | 0.080 |
| 8 | 13.7 | 105 | 120 | 5 | 0.3 | 99.7 | 0.076 |
| 9 | 11.6 | 105 | 121 | 5 | 0.3 | 99.7 | 0.076 |
| 10 | 9.1 | 105 | 121 | 5 | 0.3 | 99.7 | 0.084 |

EXAMPLE 8

The reaction product (pH = 0) obtained by reacting 2,4,6-trimethylphenol with Caro's acid was extracted with the same amount of benzene to separate an aqueous solution containing the Caro's acid. The upper benzene phase was washed with the same amount of water, and subjected to a rotary evaporator to drive off the benzene. The resulting crude TMCH was analyzed and found to contain 14.3% by weight of 2,4,6-trimethylphenol and 79.9% by weight of TMCH and have an optical density of 0.170 and a pH of 5.5.

130.5 g of this crude TMCH was distilled in the same distillation device as used in Example 2. The results obtained are shown in Table 8.

The distillation residue was black in color, and weighed 15.8 g. It was analyzed and found to contain 0.3% by weight of 2,4,6-trimethylphenol and 35.2% by weight of TMCH and have an optical density of 2. The material balance was 99.9% by weight for 2,4,6-trimethylphenol and 100.0% by weight for TMCH.

and the light yellow benzene phase at the upper part was transferred to a rotary evaporator, after which Table 8

| Weight of the distillate (g) | Temperature (°C.) Top of the still | Temperature (°C.) Bottom of the still | Pressure at the top of the still (mmHg. abs) | Analysis of the distillate TMP (wt. %) | Analysis of the distillate TMCH (wt. %) | Optical density |
|---|---|---|---|---|---|---|
| 8.5  | 87      | 115     | 5 | 97.5 | 2.5  | 0.053 |
| 10.5 | 85–104  | 115–118 | 5 | 76.5 | 23.5 | 0.210 |
| 11.0 | 104–112 | 118–122 | 5 | 14.2 | 85.5 | 0.186 |
| 13.0 | 110–114 | 120–123 | 5 | 2.8  | 97.2 | 0.098 |
| 12.5 | 112–113 | 121–123 | 5 | 0.6  | 99.4 | 0.075 |
| 11.0 | 112     | 123     | 5 | 0.4  | 99.6 | 0.074 |
| 11.2 | 110–112 | 120–122 | 5 | 0.4  | 99.6 | 0.076 |
| 15.5 | 112–113 | 120–125 | 5 | 0.3  | 99.7 | 0.075 |
| 12.0 | 113     | 125–126 | 5 | 0.7  | 99.3 | 0.072 |
| 9.5  | 110–102 | 126–133 | 5 | 0.3  | 99.7 | 0.074 |

EXAMPLE 9

1-Hydroxyamino-2,4,6-trimethylbenzene was dissolved in a 10% dilute aqueous solution of sulfuric acid at 1.5°C. in carbon dioxide gas, and the solution was stirred for 2.5 hours. The resulting reaction product was extracted with the same amount of benzene. The benzene phase was washed with water and subjected to a rotary evaporator on a warm bath a 35°C. to remove the benzene, and to obtain crude TMCH which was found to contain 7.6% by weight of 1-hydroxyamino-2,4,6-trimethylbenzene and 89.7% by weight of TMCH and have a pH of 6.9 and an optical density of 0.211.

100 g of the crude TMCH was charged into the same distillation device as used in Example 2 and distilled batchwise. The results are shown in Table 9.

The distillate was analyzed by gas-chromatography. No absorption peak ascribable to the 1-hydroxyamino-2,4,6-trimethylbenzene was observed, and three peaks ascribable to unknown substances were observed. These unknown substances have been referred to as B, C and D.

The evaporation residue weighed 6.0 g, and found to contain 25.8% by weight of TMCH, 0.3% by weight of C, and have an optical density of 2. B and D were not observed in the residue.

benzene was driven off at reduced pressure, thereby to obtain 990 g of crude TMCH.

The crude TMCH was analyzed, and found to contain 15.6% by weight of 2,4,6-trimethyl phenol and 80.1% by weight of TMCH and have an optical density of 0.161 and a pH of 6.7.

The crude TMCH was maintained at 50°C. in a stream of nitrogen, and in the molten state, continuously fed at a rate of 75 g/hour into the middle part of a distillation still (I). The distillation still (I) had a diameter of 22 mm and a length of 400 mm, and was packed with HEli-Pak No. 1. The pressure of the distillation still at its top was maintained at 10 mmHg abs., and the temperature was 95°C. at the top and 130°C. at the bottom. The reflux ratio was 49. Water at 82°C. was passed through a condenser at the top of the distillation still (I).

A liquid distillate of 2,4,6-trimethylphenol was obtained from the top of the distillation still (I) at a rate of 11.7 g/hour. This distillate was solid at room temperature, and white in color. On the other hand, from the bottom of the still, a liquid consisting mainly of TMCH was withdrawn at a rate of 63.3 g/hour, and fed continuously to a distillation still (II).

The distillation still (II) had a diameter of 22 mm and a length of 200 mm, and was packed with HEli-Pak No.

Table 9

| Samples Nos. | Weight of the distillate (g) | Temperature (°C.) Top of the still | Temperature (°C.) Bottom of the still | Pressure at the top of the still (mmHg. abs) | Analysis of the distillate TMCH (wt. %) | B (wt. %) | C (wt. %) | D (wt. %) | Optical density |
|---|---|---|---|---|---|---|---|---|---|
| 1  | 10.0 | 78 | 90.5 | 0.8 | 68.1 | 21.3 | 10.6 | 0   | 1.02 |
| 2  | 6.0  | 79 | 91.0 | 0.9 | 77.0 | 16.0 | 7.0  | 0   | 1.38 |
| 3  | 5.5  | 80 | 91.0 | 0.8 | 84.5 | 6.4  | 5.7  | 3.4 | 0.52 |
| 4  | 10.5 | 81 | 92.0 | 0.8 | 97.4 | 0.4  | 0.9  | 1.3 | 0.25 |
| 5  | 11.0 | 82 | 92.5 | 0.8 | 99.4 | 0    | 0.3  | 0.3 | 0.24 |
| 6  | 10.5 | 83 | 93   | 0.8 | 99.9 | 0    | 0.1  | 0   | 0.25 |
| 7  | 11.0 | 83 | 92.5 | 0.8 | 99.9 | 0    | 0.1  | 0   | 0.26 |
| 8  | 8.5  | 83 | 93   | 0.8 | 99.9 | 0    | 0.1  | 0   | 0.29 |
| 9  | 8.0  | 83 | 93   | 0.8 | 99.9 | 0    | 0.1  | 0   | 0.28 |
| 10 | 13.0 | 83 | 93   | 0.8 | 99.9 | 0    | 0.1  | 0   | 0.36 |

EXAMPLE 10

An autoclave was charged with 900 g of 2,4,6-trimethylphenol, 200 g of sodium hydroxide and 3,000 g of water, and oxygen was introduced into the autoclave to a partial oxygen pressure of 100 Kg/cm$^2$.G, followed by stirring for 30 minutes at 50°C. The reaction product was withdrawn, and transferred to a flask. After adding 4,000 g of benzene, it was stirred for 10 minutes, and then allowed to stand. The aqueous phase at the bottom which assumed a black brown color was discarded, 1. The pressure of the distillation still (II) at its top was maintained at 2 mmHg. abs., and the temperature was 98°C. at the top, and 150°C. at the bottom. The reflux ratio was 22.

A liquid distillate of TMCH (purified TMCH) having a light yellow color was obtained from the top of the still at a rate of 59.2 g/hour. On the other hand, the molten residue with a black color was withdrawn from the bottom of the still intermittently at a rate of 4.1 g/hour.

The results obtained are shown in Table 10.

Table 10

| Distillation still | Analysis of the distillate | | | | | |
|---|---|---|---|---|---|---|
| | Distillate from the top of the still | | | Residue from the bottom of the still | | |
| | TMP (wt. %) | TMCH (wt. %) | Optical density | TMP (wt. %) | TMCH (wt. %) | Optical density |
| I | 99.4 | 0.6 | 0.010 | 0.1 | 94.8 | 0.089 |
| II | 0.1 | 99.9 | 0.068 | trace | 7.3 | 2 |

The recovery ratio of TMCH was 98.5% by weight.

EXAMPLE 11

To the reaction product obtained by oxidation in the same way as in Example 10, each of the organic solvents indicated in Table 11 was added. After stirring the mixture for 10 minutes, it was separated into an organic solvent phase and an aqueous phase assuming a black brown color. The same organic solvent as used above was added to the aqueous phase, and the extraction was repeated twice. The organic solvent phases resulting in these extraction operations were combined, and subjected to a rotary evaporator to remove the organic solvent at reduced pressure, thereby to obtain crude TMCH. The crude TMCH was analyzed, and the results are shown in Table 11 below.

The crude TMCH so obtained was continuously distilled in the same distillation device as in Example 10. The ratio of recovery of purified TMCH was as shown in Table 11.

EXAMPLE 13

The procedure of Example 10 was repeated except that instead of the distillation still (II), a spinning band still was used. This distillation apparatus consisted of a heating section as a lower part and a distilling section as an upper part, the upper part being connected to the lower part. The upper distilling section had a diameter of 8 mm and a length of 900 mm (speed of rotation 2,500 rpm), and was provided with a condenser at its uppermost part. A liquid consisting mainly of TMCH discharged from the bottom of the distillation still (I) was continuously fed at a rate of 63.2 g/hour into the middle part of this distillation apparatus. The pressure of the distillation apparatus at its top was maintained at 760 mmHg. abs. and at a temperature of 245°C. The reflux ratio was 9. Purified TMCH was continuously obtained from the top of the distillation apparatus at a rate of 55.2 g/hour.

On the other hand, the lower heating section was

Table 11

| Organic solvent used for extraction | Analysis of crude TMCH | | | | Distillate at the top of the distillation still (I) | | Distillate at the top of the distillation still (II) | | | Recovery ratio of TMCH (wt. %) |
|---|---|---|---|---|---|---|---|---|---|---|
| | TMP (wt. %) | TMCH (wt. %) | Optical density | pH | TMP (wt. %) | TMCH (wt. %) | TMP (wt. %) | TMCH (wt. %) | Optical density | |
| n-Hexane | 15.2 | 80.1 | 0.171 | 6.7 | 99.4 | 0.6 | 0.2 | 99.8 | 0.068 | 98.2 |
| Cyclohexane | 16.3 | 82.2 | 0.166 | 6.6 | 99.5 | 0.5 | 0.1 | 99.9 | 0.072 | 97.9 |
| Carbon tetrachloride | 15.6 | 80.0 | 0.168 | 6.7 | 99.6 | 0.4 | 0.1 | 99.9 | 0.069 | 98.5 |
| Xylene | 15.7 | 80.1 | 0.180 | 6.7 | 99.3 | 0.7 | 0.7 | 99.7 | 0.068 | 98.1 |
| Perchloroethylene | 18.2 | 81.0 | 0.167 | 6.5 | 99.5 | 0.5 | 0.2 | 99.8 | 0.071 | 98.0 |
| Chlorobenzene | 15.6 | 80.2 | 0.170 | 6.7 | 99.4 | 0.6 | 0.1 | 99.9 | 0.069 | 98.4 |

EXAMPLE 12

Dilute sulfuric acid was added dropwise to the reaction mixture obtained in the same way as in Example 10 to neutralize it. The solid precipitated was separated by filtration. The solution was subjected to the same extraction procedure as in Example 10 to form crude TMCH (TMP 15.5% by weight, TMCH 80.1% by weight, optical density 0.170, pH 7.0). The crude TMCH was distilled in the same way as in Example 10. The results obtained are shown in Table 12 below.

Table 12

| | TMP (wt. %) | TMCH (wt. %) | Optical density |
|---|---|---|---|
| Distillate from the top of the distillation still (I) | 99.6 | 0.4 | — |
| Distillate at the top of the distillation still (II) (purified TMCH) | 0.1 | 99.9 | 0.070 |

The recovery ratio of TMCH was 98.5% by weight.

provided with a jacket and had a diameter of 8 mm and a length of 900 mm (the speed of rotation 2,500 rpm). The jacket was heated at 250°C. through a heat transfer medium. The still at the bottom had a capacity of 10 cc, and from it, the distillation residue was discharged intermittently at a rate of 8.0 g/hour.

The resulting purified TMCH was analyzed, and found to contain 0.9% by weight of TMP and 99.1% by weight of TMCH and have an optical density of 0.131. The recovery ratio of TMCH was 92.0% by weight.

COMPARATIVE EXAMPLE 1

An autoclave was charged with 9 g of the same crude TMCH as used in Example 1 and 100 g of distilled water, and after purging with nitrogen, heated to 130°C., followed by stirring for 20 minutes. The mixture was then cooled to 30°C. at a rate of 1.1°C./min. The solution was withdrawn, and separated into a solid and a liquid. The solid was washed with water and dried to obtain 7.0 g of TMCH which, when analyzed, was found to contain 14.28% by weight of 2,4,6-trimethyl phenol and 82.14% by weight of TMCH and have an optical density of 0.097.

Furthermore, the above recrystallizing operation was performed twice with a care taken so that the ratio of the crude TMCH and the distilled water became the same. This resulted in the formation of 5.2 g of TMCH which when analyzed, was found to contain 19.21% by weight of 2,4,6-trimethylphenol and 77.90% by weight of TMCH and have an optical density of 0.092.

It was therefore found that the optical density of the resulting TMCH increased somewhat as a result of the recrystallization from water, but the purity of TMCH rather decreased. The ratio of recovery of the recrystallized TMCH based on TMCH in the crude TMCH fed was 66.3% by weight.

COMPARATIVE EXAMPLE 2

A flask equipped with a reflux tube was charged with 5 g of the same crude TMCH as used in Example 1 and 105 g of petroleum ether, and the mixture was boiled for 60 minutes at atmospheric pressure. The reaction mixture was then cooled with dry ice-methanol. The solid was recovered, and washed with a small amount of petroleum ether, followed by drying to form 3.8 g of TMCH, which when analyzed, was found to contain 7.31% by weight of 2,4,6-trimethylphenol and 92.51% by weight of TMCH and have an optical density of 0.095.

Furthermore, the above recrystallization operation was performed twice with a care taken so that the ratio of the crude TMCH to the petroleum ether became the same. This resulted in the formation of 2.2 g of purified TMCH. Analysis showed that it contained 1.51% by weight of 2,4,6-trimethylphenol and 98.49% by weight of TMCH and had an optical density of 0.081. However, the ratio of recovery of the purified TMCH based on TMCH in the charged crude TMCH was 50.5% by weight.

What we claim is:

1. A process for recovering purified 4-hydroxy-2,4,6-trimethyl-2,5-cyclohexadien-1-one, which comprises distilling crude 4-hydroxy-2,4,6-trimethyl-2,5-cyclohexadien-1-one having a pH of 4 to 11.5 at a temperature of 60° to 200°C. and under a pressure which is equal to or less than the vapor pressure of 4-hydroxy-2,4,6-trimethyl-2,5-cyclohexadien-1-one at said distillation temperature and within the range of about 0.1 to about 180 mmHg absolute, said crude 4-hydroxy-2,4,6-trimethyl-2,5-cyclohexadien-1-one being obtained by oxidizing 2,4,6-trimethyl phenol or by rearrangement of 1-hydroxyamino-2,4,6-trimethylbenzene, and said pH value being measured by a solution obtained by dissolving 4 parts by weight of crude 4-hydroxy-2,4,6-trimethyl-2,5-cyclohexadien-1-one in an aqueous solution consisting of 10 parts by weight of methanol and 3 parts by weight of water, and recovering the purified 4-hydroxy-2,4,6-trimethyl-2,5-cyclohexadien-1-one.

2. The process of claim 1 wherein the pH value is 5 to 11.

3. The process of recovering purified 1-hydroxy-2,4,6-trimethyl-2,5-cyclohexadien-1-one according to claim 1, which comprises neutralizing a reaction mixture containing crude 1-hydroxy-2,4,6-trimethyl-2,5-cyclohexadien-1-one or treating it with an extracting solvent to form crude 1-hydroxy-2,4,6-trimethyl-2,5-cyclohexadien-1-one having a pH value of 4 to 11.5, distilling said crude 1-hydroxy-2,4,6-trimethyl-2,5-cyclohexadien-1-one, and then recovering the purified 4-hydroxy-2,4,6-trimethyl-2,5-cyclohexadien-1-one.

4. The process of claim 1 wherein said crude 4-hydroxy-2,4,6-trimethyl-2,5-cyclohexadien-1-one is obtained by oxidizing 2,4,6-trimethyl phenol.

* * * * *